US010213566B2

(12) United States Patent
Cortez, Jr. et al.

(10) Patent No.: US 10,213,566 B2
(45) Date of Patent: Feb. 26, 2019

(54) SYSTEMS AND METHODS FOR PROVIDING RESPIRATORY THERAPY WITH VARYING FLOW RATES

(71) Applicant: Vapotherm, Inc., Exeter, NH (US)

(72) Inventors: Felino V. Cortez, Jr., Bowie, MD (US); Thomas L. Miller, Stevensville, MD (US); William F. Niland, Arnold, MD (US)

(73) Assignee: VAPOTHERM, INC., Exeter, NH (US)

( * ) Notice: Subject to any disclaimer, the term of this patent is extended or adjusted under 35 U.S.C. 154(b) by 751 days.

(21) Appl. No.: 14/388,680

(22) PCT Filed: Mar. 27, 2013

(86) PCT No.: PCT/US2013/033982
§ 371 (c)(1),
(2) Date: Sep. 26, 2014

(87) PCT Pub. No.: WO2013/148754
PCT Pub. Date: Oct. 3, 2013

(65) Prior Publication Data
US 2015/0059751 A1   Mar. 5, 2015

Related U.S. Application Data

(60) Provisional application No. 61/616,600, filed on Mar. 28, 2012.

(51) Int. Cl.
*A61M 16/00* (2006.01)
*A61M 16/10* (2006.01)
(Continued)

(52) U.S. Cl.
CPC .... *A61M 16/0003* (2014.02); *A61M 16/0006* (2014.02); *A61M 16/0057* (2013.01);
(Continued)

(58) Field of Classification Search
CPC .......... A61M 16/0006; A61M 16/0069; A61M 16/204; A61M 16/0057; A61M 16/0816;
(Continued)

(56) References Cited

U.S. PATENT DOCUMENTS

| 3,794,026 A | 2/1974 | Jacobs |
| 4,637,385 A | 1/1987 | Rusz |

(Continued)

FOREIGN PATENT DOCUMENTS

| WO | WO-9640337 A1 | 12/1996 |
| WO | WO-2000064521 A1 | 11/2000 |
| WO | WO-2005011556 A2 | 2/2005 |

OTHER PUBLICATIONS

European Search Report dated Dec. 21, 2015 for PCT/US/2013033982.
International Search Report dated Jul. 4, 2013.

*Primary Examiner* — Gregory Anderson
*Assistant Examiner* — Jonathan Paciorek
(74) *Attorney, Agent, or Firm* — White & Case LLP

(57) ABSTRACT

Systems and methods for providing respiratory therapy with varying flow rates are disclosed. A system comprises a source of breathing gas, a patient interface, and a flow control device. The flow control device is configured to automatically change a rate of the flow of breathing gas. The flow control device may vary the rate of the flow of breathing gas at a frequency slower than a frequency of breathing of the patient. A method comprises coupling a patient interface to the patient, providing the flow of breathing gas to an inlet port of the patient interface, and automatically changing a rate of the flow of breathing gas with a flow control device in communication with the flow of breathing gas. The method may also comprise varying the (Continued)

rate of the flow of breathing gas at a frequency slower than a frequency of breathing of the patient.

14 Claims, 4 Drawing Sheets

(51) Int. Cl.
  *A61M 16/08* (2006.01)
  *A61M 16/20* (2006.01)
  *A61M 16/06* (2006.01)

(52) U.S. Cl.
  CPC .... *A61M 16/0069* (2014.02); *A61M 16/0816* (2013.01); *A61M 16/10* (2013.01); *A61M 16/1075* (2013.01); *A61M 16/20* (2013.01); *A61M 16/204* (2014.02); *A61M 16/0666* (2013.01); *A61M 2205/3334* (2013.01); *A61M 2205/3337* (2013.01)

(58) Field of Classification Search
  CPC .. A61M 16/10; A61M 16/1075; A61M 16/20; A61M 16/0666; A61M 2205/3334; A61M 2205/3337
  See application file for complete search history.

(56) References Cited

U.S. PATENT DOCUMENTS

| | | | | |
|---|---|---|---|---|
| 4,838,259 | A * | 6/1989 | Gluck | A61M 16/0096 128/204.21 |
| 5,134,995 | A | 8/1992 | Gruenke et al. | |
| 5,148,802 | A * | 9/1992 | Sanders | A61M 16/00 128/204.18 |
| 2005/0092322 | A1* | 5/2005 | Collins, Jr. | A61M 5/1723 128/200.26 |
| 2006/0070624 | A1* | 4/2006 | Kane | A61M 16/00 128/204.23 |
| 2006/0260611 | A1 | 11/2006 | Garber et al. | |
| 2008/0041383 | A1* | 2/2008 | Matthews | A61M 16/0051 128/204.23 |
| 2008/0121230 | A1* | 5/2008 | Cortez | A61M 16/0683 128/204.17 |
| 2008/0295839 | A1 | 12/2008 | Habashi | |
| 2010/0180895 | A1* | 7/2010 | Kwok | A61M 16/0051 128/204.23 |
| 2010/0192957 | A1* | 8/2010 | Hobson | A61M 16/0666 128/207.18 |
| 2010/0307500 | A1* | 12/2010 | Armitstead | A61B 5/087 128/204.23 |
| 2011/0162647 | A1 | 7/2011 | Huby et al. | |

* cited by examiner

SYSTEMS AND METHODS FOR PROVIDING RESPIRATORY THERAPY WITH VARYING FLOW RATES

CROSS-REFERENCE TO RELATED APPLICATIONS

This application is a United States National Stage filing under 35 U.S.C. § 371 of International Patent Application No. PCT/US13/33982, filed Mar. 27, 2013, which claims the benefit of U.S. Provisional Application No. 61/616,600, filed on Mar. 28, 2012, each of which is hereby incorporated herein by reference in its respective entirety. International Application No. PCT/US13/33982 was published under PCT Article 21(2) in English.

FIELD OF THE INVENTION

The present invention relates generally to respiratory therapy, and more particularly to systems and methods for use in providing respiratory therapy with varying flow rates.

BACKGROUND OF THE INVENTION

Patients with respiratory ailments may be administered a supplemental flow of breathing gases, such as oxygen, for example, to aid in respiration. These breathing gases are typically provided from a breathing gas supply, such as an oxygen tank, to a patient interface. The patient interface may be coupled to the breathing gas supply and in communication with a patient's nasal passages for delivery of the flow of breathing gas to the patient for nasal or oral inhalation. The flow of breathing gas provided to the patient may be selected based on the patient's inspiratory rate and the is patient's respiratory ailment.

One common patient interface is a nasal cannula. A nasal cannula typically includes one or more nasal prongs, with each prong inserted into a respective nostril during use. The nasal cannula may optionally be retained during use by looping tubing attached to the cannula over the user's ears and drawing the tubing tight under the user's chin, or may be secured to the user by some other means. A conventional nasal cannula is described in U.S. Patent Application Publication No. US 2008/0121230 A1.

Improved systems and methods for respiratory therapy are desired.

SUMMARY OF THE INVENTION

Aspects of the present invention are directed to systems and methods for providing respiratory therapy with varying flow rates.

In accordance with one aspect of the present invention, a system for providing respiratory therapy to a patient is disclosed. The system comprises a source of breathing gas, a patient interface, and a flow control device. The patient interface comprises an inlet port configured to receive a flow of breathing gas from the source of breathing gas and an outlet port configured to deliver the flow of breathing gas to the patient. The flow control device is in communication with the flow of breathing gas. The flow control device is configured to automatically change a rate of the flow of breathing gas. The flow control device may vary the rate of the flow of breathing gas at a frequency slower than a frequency of breathing of the patient.

In accordance with another aspect of the present invention, a method for providing respiratory therapy to a patient is disclosed. The method comprises coupling a patient interface to the patient, providing the flow of breathing gas to an inlet port of the patient interface, and automatically changing a rate of the flow of breathing gas with a flow control device in communication with the flow of breathing gas. The method may also comprise varying the rate of the flow of breathing gas at a frequency slower than a frequency of breathing of the patient.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale, unless otherwise indicated. To the contrary, the dimensions of the various features may be expanded or reduced for clarity. Included in the drawings are the following figures.

DETAILED DESCRIPTION OF THE INVENTION

Embodiments of the present invention are directed to systems and methods for providing respiratory therapy to a patient. These exemplary embodiments are usable to provide a flow of breathing gas to a patient at a varying rate of flow. The flow rates provided to the patient may be selected based on a number of factors, which are set forth in detail below.

While the exemplary embodiments are described herein with respect to a nasal cannula, it will be understood that other patient interfaces, such as breathing masks, may be used without departing from the scope of the invention. As used herein, the term patient interface is intended to encompass any suitable apparatus for providing a flow of breathing gas to a patient for nasal and/or oral inhalation. Suitable patient interfaces will be known to one of ordinary skill in the art from the description herein.

As a general overview, the disclosed embodiments of the present invention are usable to automatically vary the rate of a flow of breathing gas to a patient. The flow rate may vary between a predetermined maximum flow rate and a predetermined minimum flow rate The flow rate may be varied periodically at a rate slower than the patient's rate of breathing. By varying the flow rate in this way, the disclosed embodiments may be useful to vary the patient's airway pressure, and thereby change the patient's functional residual capacity (FRC). By way of a bellowing effect on the FRC, the disclosed embodiments may desirably improve alveolar ventilation.

Figure 1:
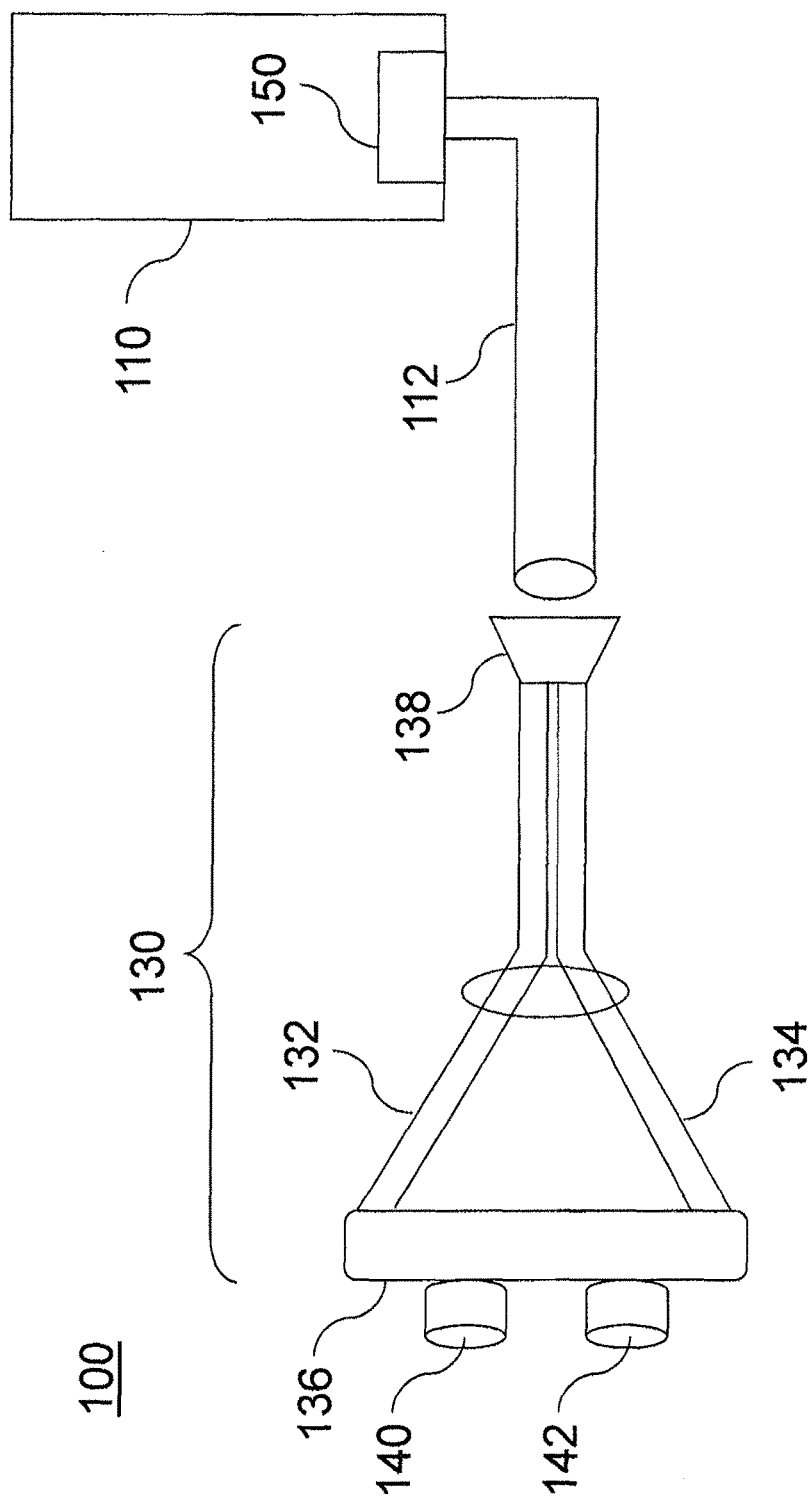
FIG. 1 is a diagram illustrating an exemplary system for providing respiratory therapy to a patient in accordance with aspects of the present invention.

Referring now to the drawings, FIG. 1 illustrates an exemplary system 100 for providing respiratory therapy to a patient in accordance with aspects of the present invention. Generally, system 100 includes a source of breathing gas 110, a patient interface (such as nasal cannula 130), and a flow control device 150. Additional details of system 100 will be described herein.

Source 110 provides breathing gas for inhalation by a patient. In an exemplary embodiment, source 110 generates heated and humidified breathing gas for delivery to the patient. As shown in FIG. 1, source 110 may include a delivery tube 112. Delivery tube 112 may be coupled to patient interface 130 in order to provide the heated and humidified gas from source 110 to the patient. Source 110 may be configured to provide breathing gas at flow rates between 4 and 8 liters per minute (lpm) for infants, or between 25 and 40 lpm for adults. Suitable sources of heated and humidified gas will be known to one of ordinary skill in the art. For example, source 110 may be the Vapotherm Flowrest System provided by Vapotherm, Inc. of Stevensville, Md., USA. Other suitable sources of breathing gas 110 will be known to one of ordinary skill in the art from the description herein.

Nasal cannula 130 is configured to deliver the flow of breathing gas from source 110 to the patient. In an exemplary embodiment, nasal cannula 130 comprises a first supply tube 132, a second supply tube 134, and a cannula body 136, as shown in FIG. 1. Supply tubes 132 and 134 are elongated, hollow lumens. Supply tubes 132 and 134 are connected to a connector 138 in order to receive breathing gas from a breathing gas source. Connector 138 defines an inlet port and is configured to be connected to delivery tube 112 of source of breathing gas 110. Thereby, supply tubes 132 and 134 enable fluid communication between source 110 and cannula body 136.

Cannula body 136 is coupled to the ends of supply tubes 132 and 134 opposite connector 138. As shown in FIG. 1, cannula body 136 includes nasal prongs 140 and 142 extending from cannula body 136. When nasal cannula 130 is secured to the patient, nasal prongs 140 and 142 are positioned within respective nares of the patient. Nasal prongs 140 and 142 define the outlet ports of nasal cannula 130, and deliver the flow of breathing gas received from supply tubes 132 and 134 to the patient. The shape and length of nasal prongs 140 and 142 may be selected to deliver pressure and/or facilitate purging of dead space, as would be understood by one of ordinary skill in the art.

Flow control device 150 disposed within system 100 is in communication with the flow of breathing gas. As shown in FIG. 1, flow control device 150 may be positioned within source of breathing gas 110. Alternatively, flow control device 150 may be coupled to or positioned within delivery tube 112 or nasal cannula 130.

Flow control device 150 is configured to automatically change a rate of the flow of breathing gas to the patient. As used herein, the term "automatically" is intended to convey that flow control device 150 is operable to change the rate of the flow of breathing gas without being caused to do so by an operator or patient of system 100. While flow control device 150 may be initially installed, prepared, or configured by such a user, during delivery of breathing gas to the patient, flow control device 150 operates to change the flow rate automatically, without direct instruction to perform such a change in flow rate.

Figure 2:
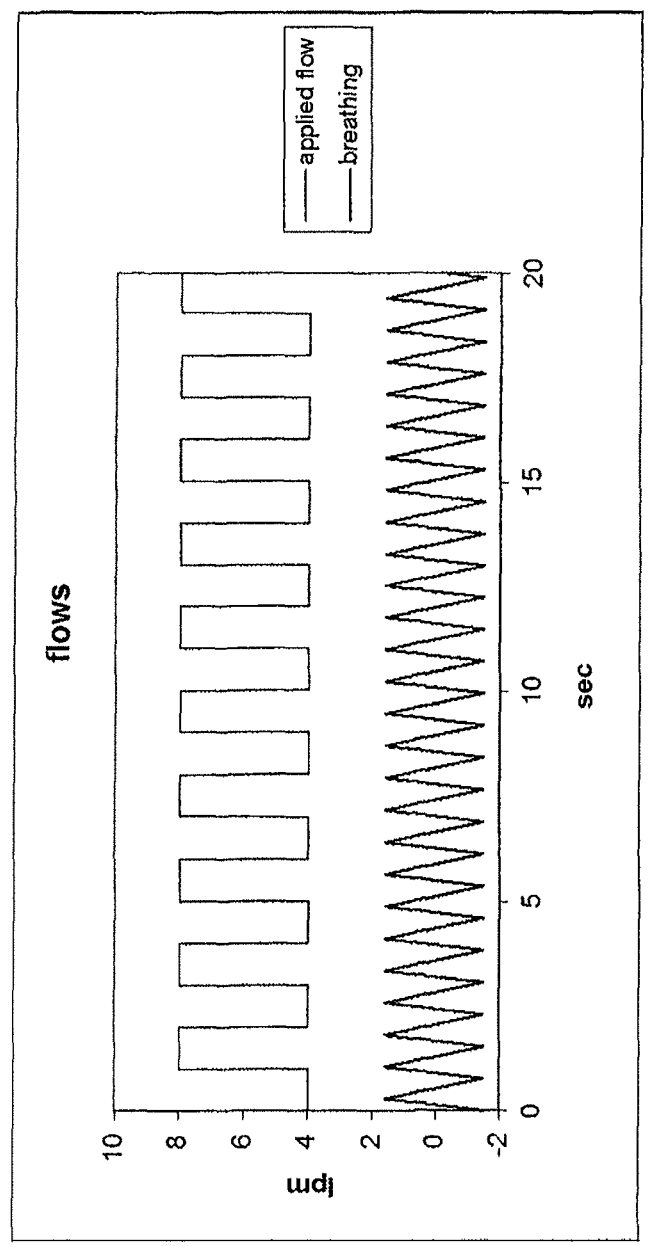
FIG. 2 is a graph illustrating flow rate over time for an exemplary operation of the system of FIG. 1.

Flow control device 150 is configured to periodically vary the flow rate between the high flow rate and the low flow rate. The frequency of the period is lower than a frequency of breathing of the patient. In other words, the variance in flow rate provided by flow control device 150 is selected to be slower than the patient's rate of breathing. In one embodiment, flow control device may vary the flow of breathing gas at a frequency of equal to or less than half of the breathing rate of the patient. This may be desirable so as to cause a change in functional residual capacity (FRC) of the patient, as opposed to an augmentation of tidal volume. Suitable frequencies for varying the flow rate between the high flow rate and the low flow rate may be chosen based on the patient's rate of breathing. For example, for infants, the changes frequency may be approximately 0.5 Hz (one cycle approximately every two seconds). In accordance with the above-described operations of flow control device 150, a graph of flow rate over time to be provided by system 100 is illustrated in FIG. 2.

In an exemplary embodiment, flow control device 150 is an oscillating fluidic flip valve. The valve is positioned in line with the flow of breathing gas. The valve includes an exhaust port for venting an excess flow of breathing gas provided by source 110. As would be understood by one of ordinary skill in the art, the valve may be configured to oscillate back and forth based on a fluid flip action, thereby allowing the patient to intermittently receive all and then some of the flow of breathing gas from source 110. Suitable valves for use as flow control device 150 include solenoid valves, auto pinch valves, or stepping motor valves. Other suitable valves will be known to one of ordinary skill in the art from the description herein.

In another exemplary embodiment, flow control device 150 comprises flow control circuitry coupled to source of breathing gas 110. The flow control circuitry is programmed to automatically change the rate of flow of breathing gas provided by source 110. The flow control circuitry may change the flow rate, for example, by adjusting the power to a flow generating element (e.g., a blower) within source 110. Alternatively, flow control circuitry may change the flow rate by adjusting a pressure of breathing gas within source 110, or adjusting the size of a breathing gas outlet of source 110 (e.g. with an adjustable/variable size orifice). Still further, flow control circuitry may change the flow rate by controlling the rate of a bypass flow to subtract from the main gas flow from source 110 (e.g., with a peristaltic or other pump). Suitable functions for flow control circuitry may be selected based on the type of source of breathing gas 110 used with system 100. Suitable processors and components for use as flow control circuitry will be known to one of ordinary skill in the art from the description herein.

In an exemplary operation, flow control device 150 is configured to maintain a first flow of breathing gas at a first flow rate for a first predetermined period of time, and then vary the flow rate in order to maintain a second flow of breathing gas at a second flow rate for a second predetermined period of time. The predetermined periods of time may be the same or different. For example, when treating infants, the first and second flow rates may be maintained for approximately one second. It may be desirable that flow control device 150 change between the flow rates as quickly as possible (e.g., in one quarter second or less). The first flow rate may be a comparatively high flow rate (e.g., 8 lpm for infants, 40 lpm for adults), and the second flow rate may be a comparatively low flow rate (e.g., 4 lpm for infants, 25 lpm for adults). It may be desirable that the low flow rate be less than approximately 50% of the high flow rate. It may also be desirable that the low flow rate still be higher than an inspiratory flow rate of the patient, in order to meet the patient's inspiratory flow needs and still have additional flow sufficient to purge the available anatomical dead space.

While only a single flow control device 150 described above, it will be understood by one of ordinary skill in the art that system 100 is not so limited. System 100 may comprise multiple flow control devices 150, positioned at various points throughout system 100, in order to vary the flow of breathing gas to the patient.

Figure 3:
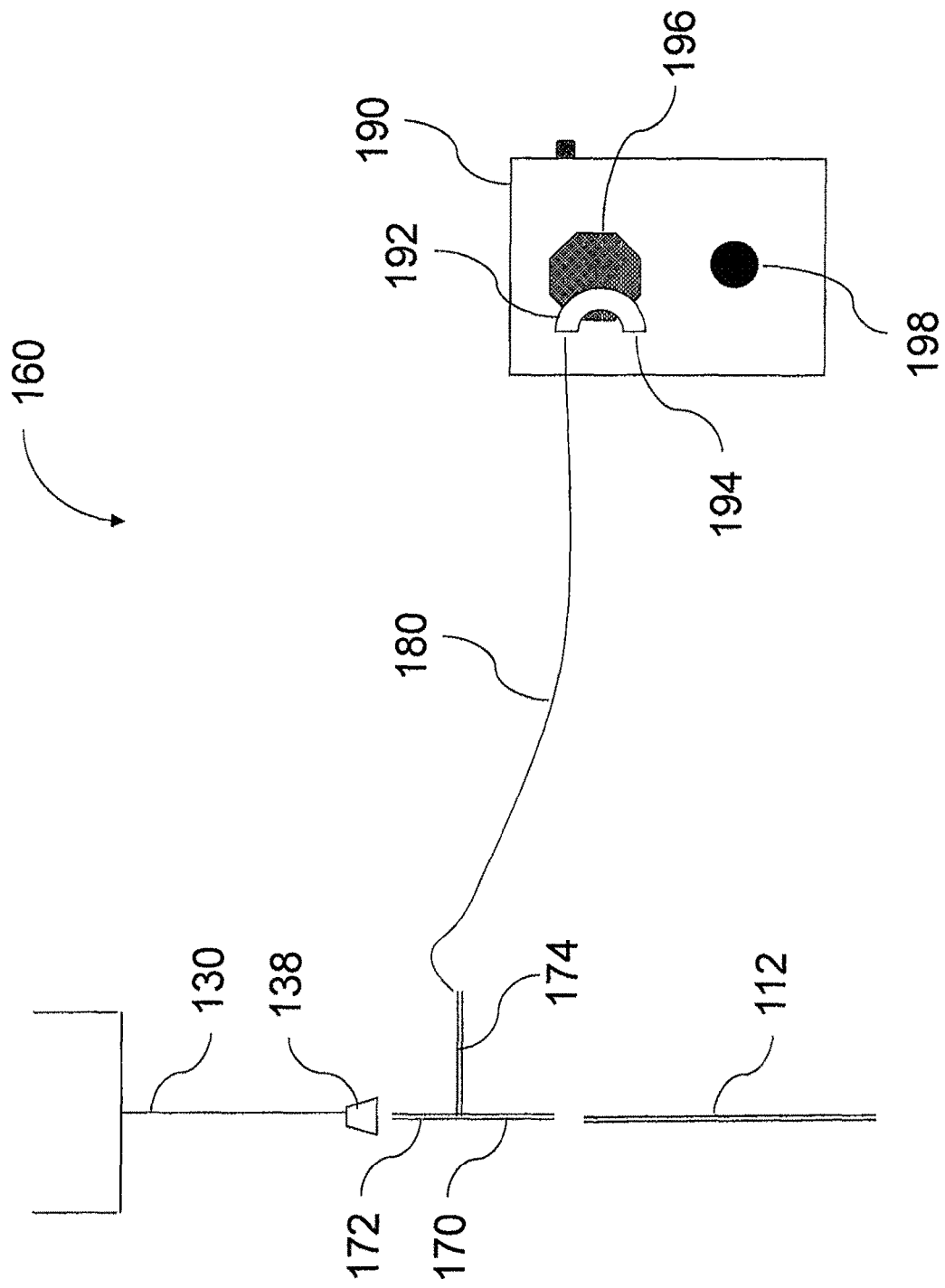
FIG. 3 is a diagram illustrating an exemplary apparatus for varying flow rate in accordance with aspects of the present invention.

FIG. 3 illustrates an exemplary apparatus 160 for varying the flow rate of breathing gas in accordance with aspects of the present invention. Apparatus 160 may be used in conjunction with the exemplary system 100 described above. Generally, apparatus 160 includes an adaptor 170, tubing 180, and a pump module 190. Additional details of apparatus 160 will be described herein.

Adaptor 170 creates a bypass line in system 100. As set forth above, system 100 includes a source of breathing gas 110 that provides a flow of breathing gas to nasal cannula 130. In an exemplary embodiment, adaptor 170 is a T-adaptor connected between the delivery tube 112 from the source of breathing gas 110 and the connector 138 of the nasal cannula 130. Adaptor 170 has a first branch 172 configured to provide at least a portion of the flow of breathing gas from source 110 to nasal cannula 130. Adaptor 170 has a second branch 174 configured to provide another portion of the flow of breathing gas (the "bypass flow") to pump module 180. The rate of the bypass flow is controlled by apparatus 160, as set forth below.

Tubing 180 is connected to the second branch 174 of adaptor 180. Tubing 180 conveys the bypass flow of breathing gas from adaptor 170 to pump module 190. In an exemplary embodiment, tubing 180 comprises a length of vinyl tubing. The length of tubing 180 may be selected based on the desired rate of the bypass flow of breathing gas, as set forth below.

Pump module 190 is connected to tubing 180. Pump module 190 controls the rate of the bypass flow of breathing gas through the second branch 174 of adaptor 170. In an exemplary embodiment, pump module 190 is a peristaltic pump having an inlet port 192 and an outlet port 194 and a roller 196.

When pump module 190 is activated, the roller 196 rotates at a preselected frequency. As roller 196 rotates, it periodically closes and opens a pathway between input port 192 and outlet port 194. When the pathway is closed, airflow between input port 192 and outlet port 194 is blocked. This prevents any bypass flow from exiting adaptor 170 through second branch 174, and results in the high flow rate of breathing gas being delivered to the patient via nasal cannula 130. When the pathway is open, air flow between input port 192 and outlet 194 is enabled. This allows bypass flow to exit adaptor 170 through second branch 174, and results in the low flow rate of breathing gas being delivered to the patient. The rate of the bypass flow is determined based on the size of the orifices of adaptor 170 (and particularly of second branch 174), the diameter of tubing 180, and the length of tubing 180. It will be understood by one of ordinary skill in the art that these variables may be selected to generate the optimal bypass flow, i.e., the optimal difference between the high flow rate and the low flow rate provided to the patient.

Pump module 190 includes adjustment means 198 for adjusting the frequency at which roller 196 rotates. In this exemplary embodiment, the frequency for varying the flow rate between the high flow rate and the low flow rate corresponds to the frequency of rotation of roller 196. Accordingly, the frequency for varying the flow rate may be changed using adjustment means 198. In an exemplary embodiment, adjustment means 198 is a turnable knob. However, alternative adjustment means 198 are envisioned, including buttons, switches, keypads, or any other similar structures. The configuration of the roller 196 may be selected to impact the ratio of time constants such that the patient is receiving full flow or partial flow.

Figure 4:
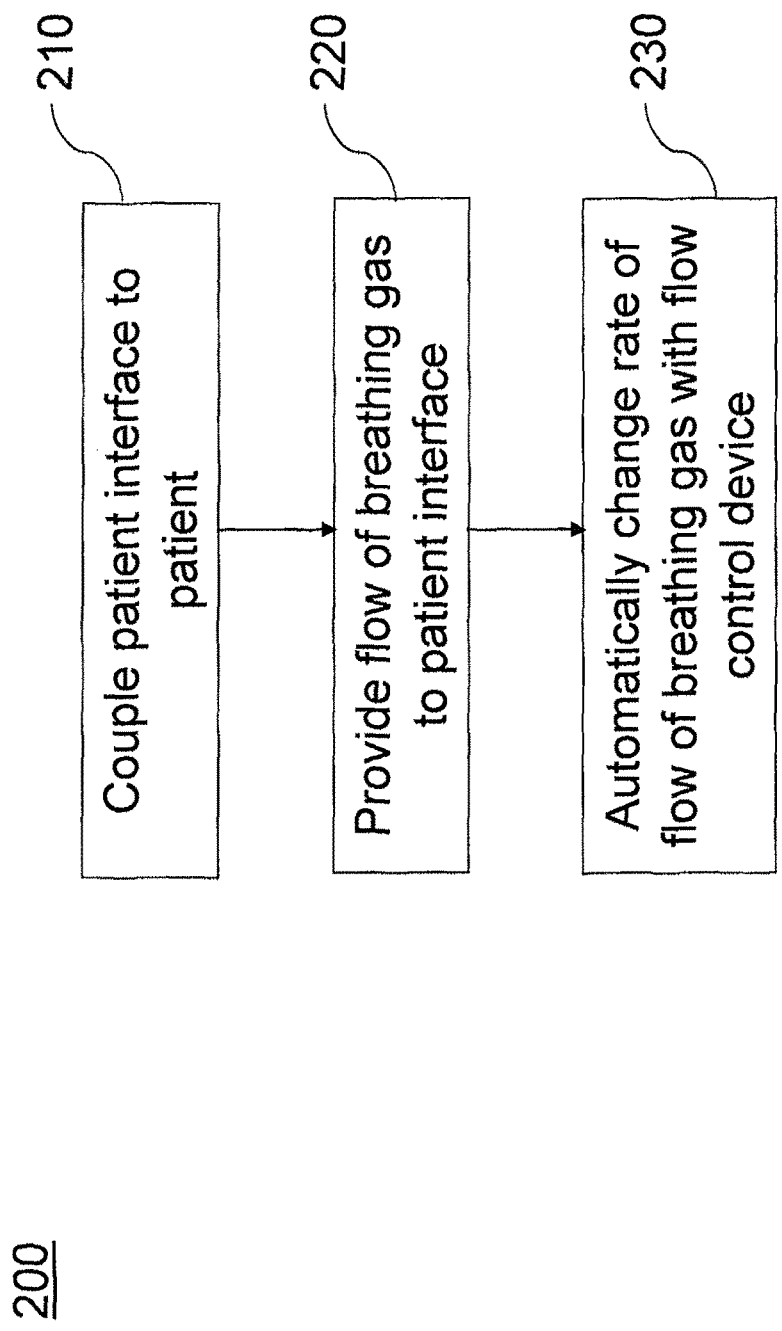
FIG. 4 is a flowchart illustrating an exemplary method for providing respiratory therapy to a patient in accordance with aspects of the present invention.

FIG. 4 is a flowchart illustrating an exemplary method 200 for providing respiratory therapy to a patient in accordance with aspects of the present invention. Method 200 may be implemented using the exemplary system 100 described above. Generally, method 200 includes coupling a patient interface to the patient, providing a flow of breathing gas, and automatically changing a rate of the flow of breathing gas. Additional details of method 200 will be described herein with reference to system 100.

In step 210, a patient interface is coupled to the patient. In an exemplary embodiment, nasal cannula 130 is secured to the patient. When nasal cannula 130 is secured to the patient, nasal prongs 140 and 142 are positioned within respective nares of the patient. Connector 138 of nasal cannula 130 may be coupled to delivery tube 112 of source of breathing gas 110 before or after nasal cannula 130 is secured to the patient.

In step 220, a flow of breathing gas is provided to the patient. In an exemplary embodiment, source 110 provides a flow of breathing gas through the inlet port defined by connector 138. The flow of breathing gas passes through supply tubes 132 and 134 to cannula body 136. The flow of breathing gas is then delivered to the patient for inhalation via nasal prongs 140 and 142.

In step 230, a rate of the flow of breathing gas is automatically changed. In an exemplary embodiment, flow control device 150 automatically changes the rate of the flow of breathing gas to the patient.

For example, step 230 may include maintaining a first flow of breathing gas at a first flow rate for a first predetermined period of time with flow control device 150, automatically varying the flow rate with flow control device 150, and maintaining a second flow of breathing gas at a second flow rate for a second predetermined period of time. The predetermined periods of time may be the same or different. The first flow rate may be a comparatively high flow rate (e.g., 8 lpm for infants, 40 lpm for adults), and the second flow rate may be a comparatively low flow rate (e.g.,4 lpm for infants, 25 lpm for adults). As set forth above, it may be desirable that the low flow rate still be higher than an inspiratory flow rate of the patient.

For another example, step 230 may include periodically varying the flow rate between the high flow rate and the low flow rate with flow control device 150. As set forth above, the frequency of the period may desirably be slower than a frequency of breathing of the patient.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for providing respiratory therapy to a patient comprising:

a source of breathing gas;

a patient interface comprising an inlet port configured to receive a flow of breathing gas from the source of breathing gas and an outlet port configured to deliver the flow of breathing gas to the patient; and a flow control device in communication with the flow of breathing gas, the flow control device configured to automatically change a rate of the flow of breathing gas, wherein the flow control device is configured to periodically vary the rate of the flow of breathing gas between a high flow rate and a low flow rate at a frequency slower than a frequency of breathing of the patient without being caused to do so by the patient, wherein the high flow rate is higher than the low flow rate, and wherein the flow control device maintains the high flow rate and the low flow rate for predetermined periods of time prior to automatically changing the rate of the flow of breathing gas.

2. The system of claim 1, wherein the patient interface comprises a nasal cannula.

3. The system of claim 1, wherein the high flow rate is 8 lpm.

4. The system of claim 1, wherein the low flow rate is higher than an inspiratory flow rate of the patient.

5. The system of claim 1, wherein the flow control device is configured to periodically vary the rate of the flow of breathing gas.

6. The system of claim 5, wherein the flow control device varies the rate of the flow of breathing gas at a frequency slower than a frequency of breathing of the patient.

7. The system of claim 1, wherein the flow control device comprises an apparatus adapted to vary a rate of a bypass flow of gas from the source of breathing gas.

8. The system of claim 7, wherein the flow control apparatus comprises a peristaltic pump configured to periodically open and close a pathway, the pathway confining at least in part the bypass flow of gas.

9. The system of claim 1, wherein the flow control device comprises an oscillating fluidic flip valve positioned in line with the flow of breathing gas.

10. The system of claim 1, wherein the flow control device comprises flow control circuitry coupled to the source of breathing gas, the flow control circuitry programmed to change the rate of the flow of breathing gas from the source of breathing gas.

11. A method for providing respiratory therapy to a patient comprising:

coupling a patient interface to the patient, the patient interface comprising an inlet port configured to receive a flow of breathing gas and an outlet port configured to deliver the flow of breathing gas to the patient;

providing the flow of breathing gas to the inlet port of the patient interface; and automatically changing a rate of the flow of breathing gas with a flow control device in communication with the flow of breathing gas, wherein the flow control device is configured to periodically vary the rate of the flow of breathing gas between a high flow rate and a low flow rate at a frequency slower than a frequency of breathing of the patient without being caused to do so by the patient, wherein the high flow rate is higher than the low flow rate, and wherein the flow control device maintains the high flow rate and the low flow rate for predetermined periods of time prior to automatically changing the rate of the flow of breathing gas.

12. The method of claim 11, wherein the coupling step comprises securing a nasal cannula to the patient.

13. The method of claim 11, wherein the high flow rate is 8 lpm.

14. The method of claim 11, wherein the low flow rate is higher than an inspiratory flow rate of the patient.

* * * * *